United States Patent [19]

Hitzman

[11] Patent Number: 4,519,984
[45] Date of Patent: May 28, 1985

[54] APPARATUS FOR CARRYING OUT SPARGED REACTION

[75] Inventor: Donald O. Hitzman, Bartlesville, Okla.

[73] Assignee: Phillips Petroleum Company, Bartlesville, Okla.

[21] Appl. No.: 340,147

[22] Filed: Jan. 18, 1982

[51] Int. Cl.³ .............................................. B01J 1/00
[52] U.S. Cl. .................................... 422/196; 435/313
[58] Field of Search ............... 422/197, 140, 200, 203, 422/231, 196, 132; 435/313

[56] References Cited

U.S. PATENT DOCUMENTS

| | | | |
|---|---|---|---|
| 3,547,188 | 12/1970 | Kuhnlein | 422/197 X |
| 3,779,711 | 12/1973 | Gryaznov et al. | 422/196 X |
| 4,256,783 | 3/1981 | Takada et al. | 422/197 |
| 4,269,805 | 5/1981 | Schoengen et al. | 422/231 |

Primary Examiner—Ferris H. Lander

[57] ABSTRACT

Apparatus for carrying out a sparged reaction, including one or a plurality of vertically-disposed reaction tubes, means for introducing a sparging gas under pressure into the bottom of the tube, means for separating and withdrawing the sparging gas from the top of the tube and means for passing the separated sparging gas in indirect heat exchange with at least part of the outside surface of the tube. The apparatus is particularly suitable for carrying out an exothermic reaction, such as a fermentation reaction for the production of single cell protein, in which the bottom of a plurality of reaction tubes are disposed in a water bath, the withdrawn sparging gas is sprayed across the tops of the tubes, preferably after reducing the pressure to cool the same, and water is withdrawn from the bath and passed downwardly along the outside of the tubes.

21 Claims, 5 Drawing Figures

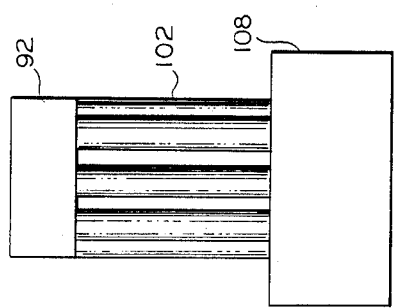
FIG. 4
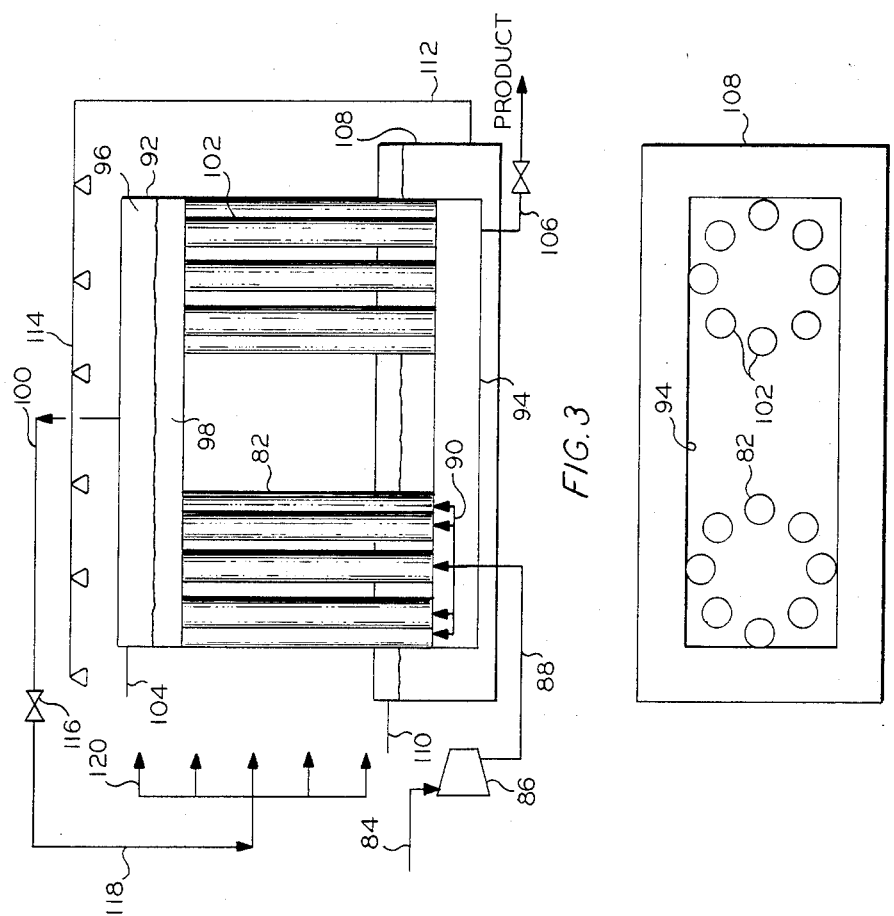
FIG. 3
FIG. 5

4,519,984

APPARATUS FOR CARRYING OUT SPARGED REACTION

The present invention relates to a method and apparatus for carrying out a sparged reaction. In a more specific aspect, the present application relates to a method and apparatus for carrying out a sparged, exothermic reaction.

BACKGROUND OF THE INVENTION

In the conduct of a number of processes, it is often necessary to agitate liquid reactants themselves or liquid reactants containing a dispersed medium, such as a catalyst in certain chemical reactions, or bacteria and yeast in a fermentation reaction in order to aid mixing and, in some cases, reduce the necessary residence time within the reactor. One convenient method of carrying out such agitation is by sparging the reaction mixture with gas under pressure. In some cases, the gas under pressure enters into the reaction, for example, in a fermentation reaction. Equipment for carrying out such sparged reactions usually consists of a vertically disposed vessel, operated in a batch or continuous manner, with means for introducing a sparging gas at the bottom of the vessel. It passes upwardly through the liquid in the vessel and is then separated at the top of the vessel and discharged. One difficulty with such reactors is that, whether operated batch-wise or continuously, it is necessary to shut down the operation in order to clean or otherwise treat the interior of the reactor. In addition, in some cases, a substantially constant temperature needs to be maintained in the vessel by indirect heat exchange. Where a single vessel of this type is utilized, the limited available heat transfer surface of the vessel makes it difficult to achieve a uniform temperature throughout the vessel. In addition, substantial amounts of energy are necessary to circulate the colling or heating fluid about the vessel, or through coils disposed within the vessel. For example, in the production of single-cell protein for human and animal consumption, bateria and yeast are fed to a fermentation vessel with a suitable substrate, such as a hydrocarbon, polysaccharide, alcohol and the like, while oxygen is introduced into the vessel. Such a process is highly exothermic. Since the bacteria or yeast can grow only within a narrow temperature range, the liberated heat needs to be removed continuously and effectively. Conventionally, this is accomplished by circulating cooling fluid through coils in the fermentation vessel and enclosing the vessel with a cooling jacket. Such equipment requires a high pressure pump to circulate the cooling fluid and consequently, a large amount of energy.

It is an object of the present invention to overcome the above and other disadvantages of the prior art. Another object of the present invention is to provide an improved method and apparatus for carrying out a sparged reaction. A further object of the present invention is to provide an improved method and apparatus for carrying out a sparged reaction requiring the addition or removal of heat to the reactor. A still further object of the present invention is to provide an improved method and apparatus for carrying out an exothermic, sparged reaction. Yet another object of the present invention is to provide and improved method and apparatus for carrying out an exothermic sparged reaction with a minimum of energy consumption. Another object of the present invention is to provide a method and apparatus for carrying out a sparged reaction in which heat is added to and/or removed from the reaction vessel at a high rate of efficiency. These and other objects of the present invention will be apparent from the following detailed description when read in conjunction with the drawings.

SUMMARY OF THE INVENTION

The present invention relates to a method and apparatus for carrying out a sparged reaction wherein the reaction media is disposed in a plurality of spaced apart reaction tubes, a sparging gas is introduced into the bottom of said tubes, the reaction media is is separated from the sparging gas in a header common to all of said reaction tubes, the reaction media is then passed downwardly through a plurality of tubes spaced from one another and forming a downcomer bundle and passed into a common header at the bottom of said downcomer tubes and in open communication wth the bottoms of the reaction tubes. In a preferred embodiment, a heat exchange medium, preferably the separated sparging gas is circulated through at least a part of the bundle of reaction tubes. In a further embodiment the reactor is cooled by expanding the separated sparging gas to reduce the temperature thereof and the thus expanded sparging gas is then passed in indirect heat exchange with the exterior of the reactor.

BRIEF DESCRIPTION OF THE DRAWINGS

FIG. 3 shows a schematic view of yet another apparatus suitable for carrying out the process of the present invention. FIG. 4 is an end view of the apparatus in FIG. 3. FIG. 5 is a cross-sectional view taken along line 5—5 of FIG. 3.

DESCRIPTION OF THE PREFERRED EMBODIMENTS

While specific processes and equipment and arrangements of equipment are hereinafter described, it is to be understood that alternative techniques, equivalent equipment and equivalent arrangements will be apparent to one skilled in the art and the description hereinafter is to be by way of illustration and the disclosure of the best mode of the present invention and is not to be considered limiting.

Figure 1:
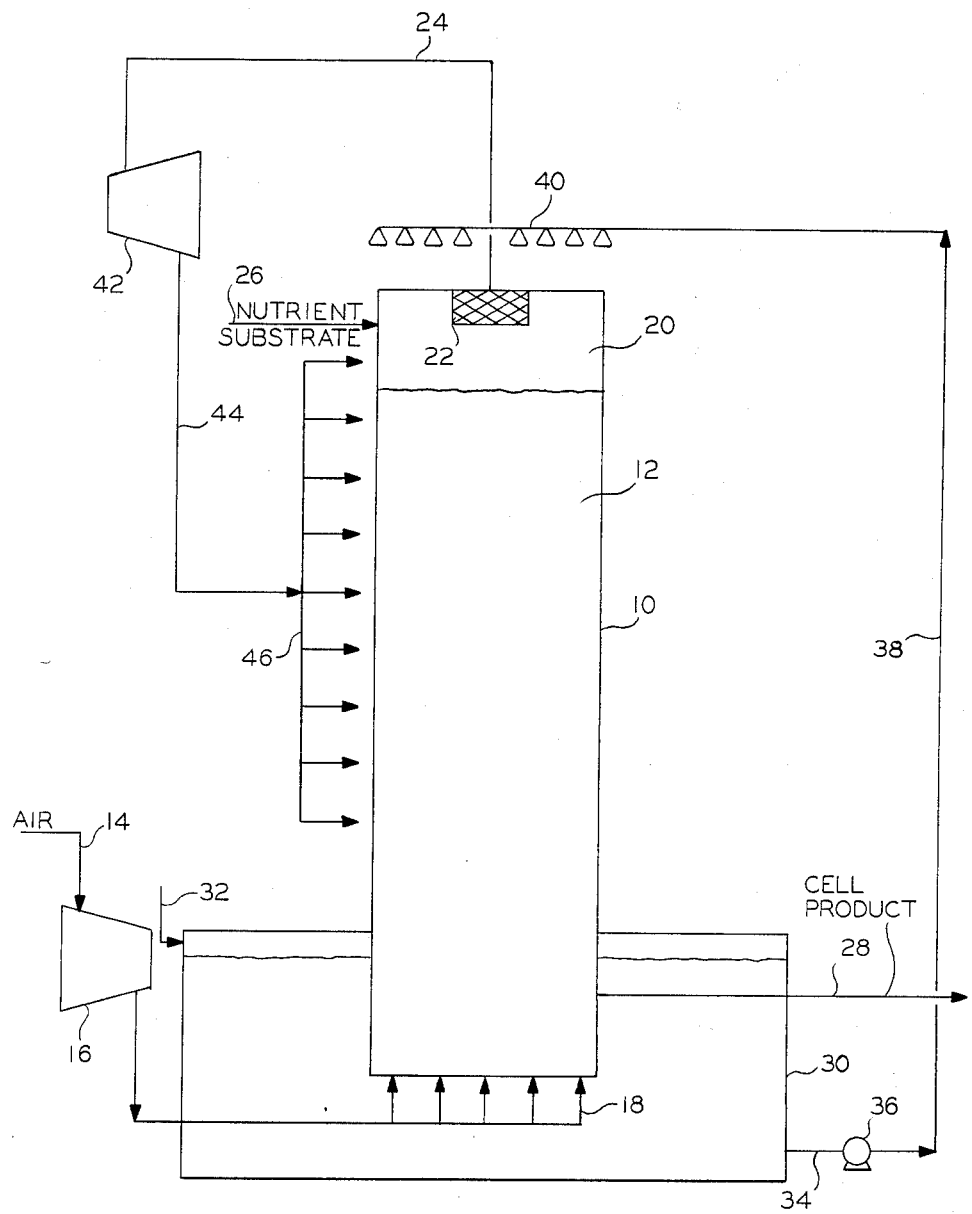
FIG. 1 of the drawings schematically shows a reaction system for carrying out the process in accordance with the present invention.

FIG. 1 schematically shows one system for carrying out a sparged process in accordance with the present invention. In FIG. 1, a vertically disposed reaction vessel 10 is partially filled with a reaction media 12, in the exemplified case a nutrient substrate containing bacteria or yeast. The reaction media 12 is sparged by introducing a gas in the particular example air or an oxygen containing gas, through line 14, thence through a compressor 16 and finally through a distribution means 18 operatively connected with the bottom of vessel 10. Above the reaction media 12, in vessel 10, is a void space 20 provided to permit separation of the sparging gas from the reaction media. The gas is passed through a suitable foam breaker 22 and thence out of vessel 10 through line 24. Where a continuous operation is conducted, nutrient substrate is introduced at the top of vessel 10 through line 26 and cell mass or cell product is withdrawn from vessel 10 through line 28. Since, in the illustrated example, a fermentation reaction is being carried out, which is highly exothermic, and the bacteria or yeast can grow only within a narrow temperature range, it is necessary that heat be extracted from the reaction vessel in order to maintain the reaction media at a constant temperature and within a narrow temperature range. For this purpose, the bottom of vessel 10 is disposed in a water reservoir 30 in which water is introduced through line 32 and withdrawn through line 34. The water withdrawn through line 34 is then pumped by means of pump 36 through line 38 to a distribution means 40 located above vessel 10. This water is then utilized as a cooling medium, preferably as a falling film about the outside of vessel 10. In order to conserve energy in the cooling of vessel 10 and the reaction media therein, the sparging gas withdrawn through line 24 is used as at least a portion of the means for cooling vessel 10. Specifically, sparging gas withdrawn through line 24 is generally at a temperature about equal to the temperature of the reaction media 12 in vessel 10. Consequently, in order to provide a cooling effect, the sparging gas is isotropically expanded through a turbine 42. Turbine 42 may be mechanically coupled to compressor 16 to thereby provide at least a part of the energy necessary for operation of the compressor or to pump 36 for circulating the cooling water. The expanded gas from expander 42 has, of course, been reduced in temperature and in relative humidity. Accordingly, it serves as a convenient method of cooling the exterior of vessel 10 both by the lower temperature of the gas, as well as aiding in the cooling by the falling film of water on the outside of the vessel.

Figure 2:
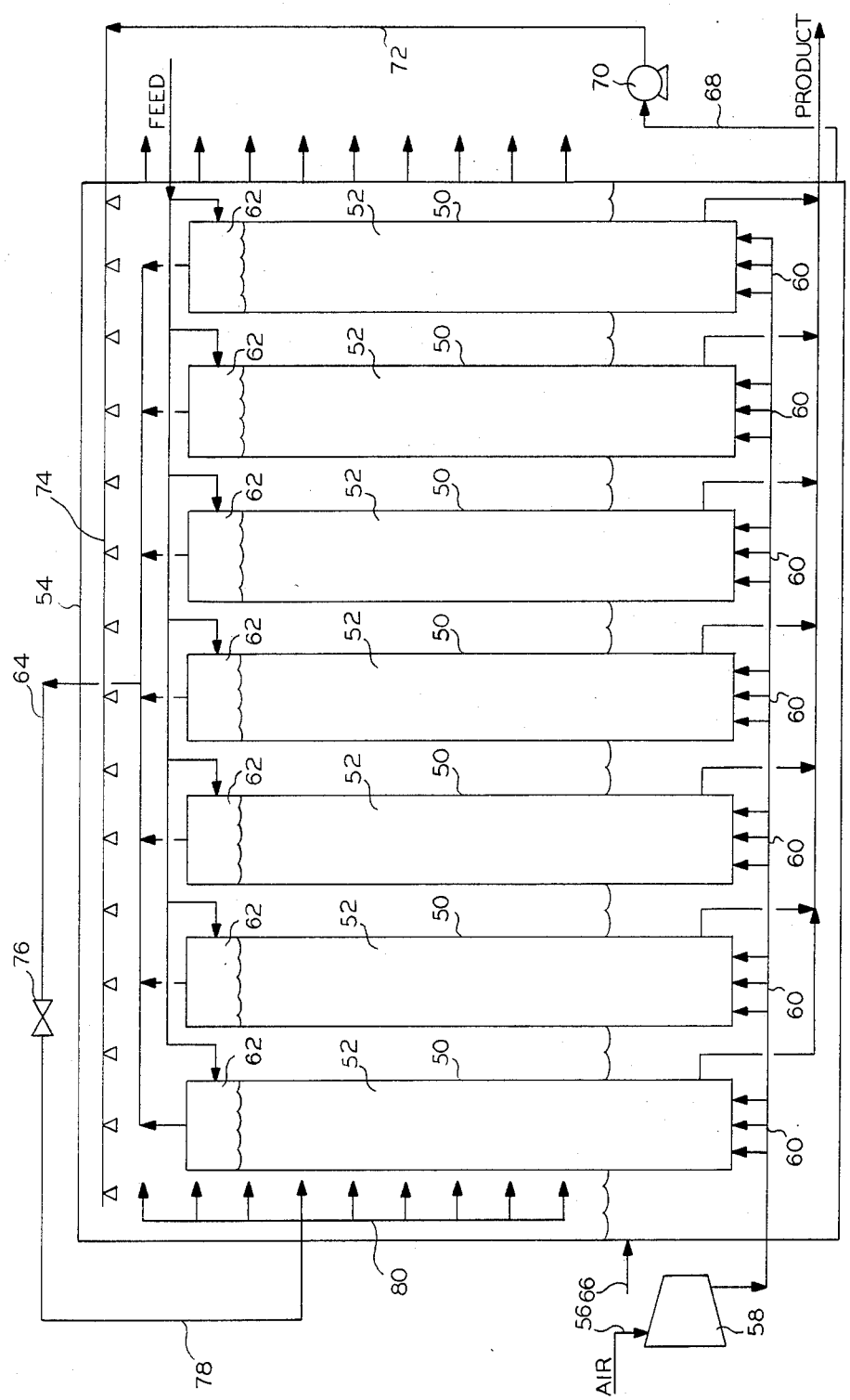
FIG. 2 of the drawings schematically shows another form of apparatus suitable for carrying out the process of the present invention.

FIG. 2 of the drawings shows schematically a variation of the system of FIG. 1. In accordance with FIG. 2, a plurality of vertically disposed reaction vessels 50 are partially filled with reaction media 52. Reactors 50 are disposed within a common outer chamber 54. Air or another sparging gas is introduced through line 56, compressed by means of a compressor 58 and introduced into the individual reactors 50 by distribution means 60. A void space 62 is maintained at the top of each of the vessels 50 for the separation of the sparging gas from the reaction media. The separated sparging gas is then withdrawn through line 64. Cooling of the vessels 50 is partially performed by introducing cooling water into the bottom of chamber 54 through line 66 and withdrawing water through line 68. The withdrawn water through line 68 is then passed through pump 70, through line 72 and thence through distribution means 74 located above the reaction vessels 50. The water then descends, preferably as a falling film, over the exterior of reaction vessels 50 thereby providing one means of cooling the same. Additional cooling is attained by adiabatically expanding the separated sparging gas through a throttle valve 76, passing the expanded gas through line 78 to an appropriate distribution means 80 within chamber 54. The cooling gas then passes through and around the reaction vessels 50 to cool the same and exits from chamber 54, preferably through openings in the wall of chamber 54.

FIGS. 3, 4 and 5 of the drawings schematically illustrate a preferred embodiment of apparatus for carrying out a sparging reaction in accordance with the present invention. In this particular instance, a plurality of vertically disposed tubes are formed into a bundle 82 of reaction tubes. Sparging gas is introduced through line 84 compressed in compressor 86, the compressed gas is passed through line 88 to distribution means 90, which introduce the sparging gas into the bundle of reactor tubes 82. Reactor tubes 82 are in open communication with an upper header 92 and a lower header 94. The upper header 92 is provided with sufficient void space 96 above the level of reaction media 98 to permit separation of the sparging gas from the reaction media. The separated sparging gas is then discharged through line 100. Upper header 92 and lower header 94 are in open communication with a bundle of downcomer tubes 102. As a result, a loop-type reactor is provided wherein the reaction media circulates through the bundle of reaction tubes 82, the upper header 92, the bundle of downcomer tubes 102, the lower header 94 and thence upwardly through the bundle of reactor tubes 82. In a continuous operation, the reaction media may be introduced through line 104 in upper header 92 and product discharged through line 106 connected to lower header 94, in a manner similar to the previously described apparatus. Partial cooling is attained by maintaining at least a portion of the lower header 94 and/or the bundles of tubes 82 and 102 in a circulating water bath 108. Water introduced into bath 108 through line 110 is withdrawn through line 112 and discharged through distribution means 114. Distribution means 114 is adapted to discharge the water about the two bundles 82 and 102 as a falling film about the tubes. Also, in accordance with the previous examples, the compressed sparging gas withdrawn through line 100 is adiabatically expanded through throttle valve 116, passed through line 118 and thence to distribution means 120. Distribution means 120 is adapted to pass the expanded sparging gas through and about the bundles of tubes 82 and 102. This particular apparatus has a number of distinct advantages, particularly in carrying out a reaction requiring indirect heat exchange for heating or cooling the reaction media. By providing bundles of tubes 82 and 102 as opposed to a single reaction vessel, a substantial increase in the cooling surface area is provided and improved efficiency and cooling results. In addition, the apparatus allows for easy scale up and tubular reactors and downcomers may be removed for servicing without interrupting the reaction.

By way of illustrative example, a fermentation vessel, such as vessel 10 of FIG. 1 may vary in diameter from about 0.5 to 3 inches and in length from 3 to 15 feet, preferably about 10 feet. A large volume of air is needed to provide oxygen for the fermentation reaction and turbulence inside the tube. For example, it is not uncommon to supply 500,000 cubic feet of air per ton of cell mass produced. The cooling effect of the withdrawn sparging air is also quite effective, for example, adiabatic expansion of the air from about 15.7 psia to 14.7 psia and evaporation of some of the water into the unsaturated air can reduce the air temperature from about 122° to 89.5° F. This cooled air is then heat exchanged with the fermentation media to reduce its temperature from about 270° F. to about 120° F. Consequently, by utilizing the sparging air and expanding the same, it is possible to remove from about 70 to 100 percent of the unwanted heat liberated during a fermentation reaction.

A suitable fermentation process which can be carried out in accordance with the present invention includes aerobic fermentation, using either bacteria or yeast as a micro organism and carbohydrates (e.g. sugar, alcohol, etc.) or hydrocarbon for a substrate feedstock for the production of alcohols, ketones, esters, aldehydes, vinegar, beer or protein. The invention can also be applied for the biotreatment of waste streams, such as a sewage stream.

By way of further example in connection with the apparatus of FIGS. 3, 4 and 5, a fermentation unit may consist of 50 2-inch i.d. 10' long tubular reactors forming the reactor bundle. The water reservoir would have a total capacity of about 300 liters. Utilizing alcohol as a substrate, the alcohol would be introduced at a rate of two liters per minute. Yeast, when used as a micro organism, grows best at a temperature environment of about 86° F. At a yeast productivity of two grams per liter per hour, 3600 kcal/hr. of heat is generated which needs to be removed to maintain the broth at a temperature of about 86° F. Compressed air at about 45 psig is injected into the unit at a rate of about 300 liters per minute to support yeast growth. The used, or separated, sparging air is exhausted from the top of the vessel at about 90% relative humidity and adiabatically expanded to near one atmosphere at 50% relative humidity. The expanded air then passes over the two bundles, cooling the fermentation broth, absorbs humidity by vaporizing the downflowing film of water on the outside of the tubes, thus maintaining the tubes at about 86° F. and the air then exits the two bundles fully saturated at a temperature of about 86° F. Cooling water is continuously pumped from the bottom of the reservoir to the top of the tubular reactor to form a continuous falling film along the outside surface of the reactors at a rate of about 20 liters per minute. Product yeast may be withdrawn continuously at a rate of about 600 grams per hour.

While specific examples have been set forth herein, it is to be understood that such examples are illustrative only and are not to be considered limiting.

I claim:

1. Apparatus for carrying out a sparged reaction, comprising:
   (a) a plurality of vertically-disposed, spaced reaction tubes forming a bundle of said reaction tubes;
   (b) a plurality of vertically-disposed, spaced downcomer tubes forming a bundle of said downcomer tubes and laterally spaced from said bundle of reaction tubes;
   (c) an upper header in open communication with the tops of said reaction tubes and the tops of said downcomer tubes;
   (d) a bottom header in open communication with the bottoms of said reaction tubes and the bottoms of said downcomer tubes;
   (e) sparging gas introduction means operatively connected to the bottoms of said reaction tubes and adapted to introduce said sparging gas, under pressure, into said reaction tubes; and
   (f) means for separating and withdrawing said sparging gas from the upper portion of said upper header.

2. Apparatus in accordance with claim 1 which additional includes means for introducing a reaction media into said upper header and means for withdrawing reaction product from said lower header.

3. Apparatus in accordance with claim 1 which additionally includes means for passing the separated sparging gas in indirect heat exchange with at least said reaction tubes.

4. Apparatus in accordance with claim 3 wherein the means for passing the separated sparging gas in indirect heat exchange with at least the reaction tubes is means for passing said separated sparging gas horizontally across at least said reaction tubes.

5. Apparatus in accordance with claim 3 wherein the means for passing the separated sparging gas in indirect heat exchange is adapted to pass the separated sparging gas in indirect heat exchange with both the reaction tubes and the downcomer tubes.

6. Apparatus in accordance with claim 5 which additionally includes expansion means adapted to expand the separated sparging gas prior to passing said sparging gas in indirect heat exchange with the reaction tubes.

7. Apparatus in accordance with claim 1 which additionally includes means for maintaining a body of circulating liquid heat exchange media in indirect heat exchange with at least the lower header.

8. Apparatus in accordance with claim 1 which additionally includes means for maintaining a circulating body of liquid heat exchange material in indirect heat exchange with the lower header and the bottom portions of said reaction tubes and said downcomer tubes.

9. Apparatus in accordance with claim 7 in which at least a portion of the liquid heat exchange material is withdrawn from the means for maintaining the body of liquid heat exchange material and additionally includes means for passing said withdrawn liquid heat exchange material in indirect heat exchange with at least said reaction tubes.

10. Apparatus in accordance with claim 8 or 9 which additionally includes means for withdrawing at least a portion of the body of liquid heat exchange material from the means for maintaining said body of liquid heat exchange material and means for passing the thus withdrawn liquid heat exchange material in indirect heat exchange with the reaction tubes and the downcomer tubes.

11. Apparatus in accordance with claim 9 wherein the means for passing the withdrawn liquid heat exchange material in indirect heat exchange with at least the reaction tubes is means for passing said withdrawn liquid heat exchange material downwardly in indirect heat exchange with at least said reaction tubes and back to the means for maintaining a body of said liquid heat exchange material.

12. Apparatus in accordance with claim 11 wherein the means for passing the separated sparging gas in indirect heat exchange with at least the reaction tubes is means for passing said separated sparging gas horizontally across at least said reaction tubes.

13. Apparatus in accordance with claim 12 which additionally includes means for introducing reaction media into the upper portion of the reaction chamber and means for withdrawing reaction product from said reaction chamber adjacent the bottom thereof.

14. Apparatus in accordance with claim 12 which additionally includes means for expanding the separated sparging gas prior to passing the same to the means for passing said separated sparging gas in indirect heat exchange with the reaction chamber.

15. Apparatus in accordance with claim 12 which additionally includes means for maintaining a body of liquid heat exchange material in contact with the outside surface of the lower portion of the reaction chamber.

16. Apparatus in accordance with claim 15 which additionally includes means for withdrawing at least a portion of the liquid heat exchange material from the body of liquid heat exchange material and means for passing the thus withdrawn liquid heat exchange material in indirect heat exchange with the outside surface of at least the upper portion of the reaction chamber.

17. Apparatus in accordance with claim 15 wherein the means for passing the withdrawn liquid heat exchange material in indirect heat exchange with the reaction chamber is means for passing said withdrawn liquid heat exchange material downwardly in indirect heat exchange with the outside surface of said reaction chamber and back to said means for maintaining the body of said heat exchange material.

18. Apparatus in accordance with claim 17 wherein the means for passing the separated sparging gas in indirect heat exchange with the reaction chamber is means for passing said separated sparging gas horizontally across the outside surface of said reaction chamber.

19. Apparatus for carrying out a sparged reaction, comprising:
  (a) at least one vertically disposed reaction chamber having gas-impermeable walls;
  (b) means for introducing a sparging gas under pressure into the bottom of said reaction chamber;
  (c) means for separating and withdrawing said sparging gas from said reaction chamber adjacent the upper end thereof; and
  (d) means for passing the thus separated sparging gas in indirect heat exchange with the outside surface of at least the upper portion of said reaction chamber.

20. Apparatus in accordance with claim 19 which includes a plurality of reaction chambers and the means for introducing sparging gas into the reaction chamber is adapted to introduce said sparging gas into all said reaction chambers, the means for withdrawing sparging gas is adapted to withdraw separated sparging gas from all of the reaction chambers and the means for passing said withdrawn sparging gas into indirect heat exchange with said reaction chamber is adapted to pass the same in indirect heat exchange with all of said reaction chambers.

21. Apparatus in accordance with claim 19 wherein the means for passing the separated sparging gas in indirect heat exchange with the reaction chamber is means for passing said separated sparging gas horizontally across the outside surface of said reaction chamber.

* * * * *